(12) United States Patent
Hershey (10) Patent No.: US 8,868,188 B2
(45) Date of Patent: Oct. 21, 2014

(54) METHOD FOR TREATING HYPERTENSION VIA ELECTRICAL STIMULATION OF NEURAL STRUCTURES

(71) Applicant: Boston Scientific Neuromodulation Corporation, Valencia, CA (US)

(72) Inventor: Bradley L. Hershey, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/026,646

(22) Filed: Sep. 13, 2013

(65) Prior Publication Data

US 2014/0081345 A1      Mar. 20, 2014

Related U.S. Application Data

(60) Provisional application No. 61/703,609, filed on Sep. 20, 2012.

(51) Int. Cl.
*A61N 1/00* (2006.01)
*A61N 1/36* (2006.01)

(52) U.S. Cl.
CPC ............. *A61N 1/36117* (2013.01); *A61N 1/36* (2013.01)
USPC ................................................ 607/30; 607/5

(58) Field of Classification Search
USPC ..................................................... 607/5, 30
See application file for complete search history.

(56) References Cited

U.S. PATENT DOCUMENTS

| | | | |
|---|---|---|---|
| 6,895,280 B2 | 5/2005 | Meadows et al. | |
| 7,650,184 B2 | 1/2010 | Walter | |
| 8,019,439 B2 | 9/2011 | Kuzma et al. | |
| 2007/0150036 A1 | 6/2007 | Anderson | |
| 2007/0168004 A1 | 7/2007 | Walter | |
| 2007/0168007 A1 | 7/2007 | Kuzma et al. | |
| 2010/0298898 A1* | 11/2010 | Libbus | 607/5 |

OTHER PUBLICATIONS

Botdorf, J. et al., Hypertension in Cadiovascular and Kidney Disease, Cardiorenal Med 2011, 1(3):183-192.
Dibona, G.F. et al., Translational medicine: the antihypertensive effect of renal denervation, Am J Physiol Regul Integr Comp Physiol 298(2): R245-R253 (2010).
Egan, B.M. et al., US Trends in Prevalence, Awareness, Treatment, and Control of Hypertension, 1988-2008, JAMA, 303(20): 2043-2050 (May 26, 2010).
Fields, L.E. et al., The Burden of Adult Hypertension in the United States 1999 to 2000: A Rising Tide, Hypertension, 44(4): 398-404 (2004).

(Continued)

*Primary Examiner* — Nicole F Lavert
(74) *Attorney, Agent, or Firm* — Vista IP Law Group LLP (57) ABSTRACT

A neuromodulation system comprises a sensor configured for sensing a blood pressure of a patient, modulation output circuitry configured for conveying electrical modulation energy to at least one electrode, and a controller/processor coupled to the sensor and the modulation output circuitry. The controller/processor is configured for comparing the blood pressure sensed by the sensor to a first threshold blood pressure, and instructing the modulation output circuitry to convey the electrical modulation energy to the at least one electrode if the sensed blood pressure is greater than the first threshold blood pressure. A method for treating chronic hypertension comprises applying electrical modulation energy to a neural target site, thereby modulating an afferent nerve innervating a patient's kidney, thereby treating the chronic hypertension.

25 Claims, 9 Drawing Sheets

(56) References Cited

OTHER PUBLICATIONS

Hajjar, I. et al., Trends in Prevalance, Awareness, Treatment, and Control of Hypertension in the United States, 1988-2000, JAMA, 290(2):199-206 (Jul. 9, 2003).

Katholi, R. E. et al., The Role of Renal Sympathetic Nerves in Hypertension: Has Percutaneous Renal Denervation Refocused Attention on Their Clinical Significance?, Prog Cardiovasc Dis 52(3): 243-248 (2009).

Larkin, T.M. et al., Acute Renal Failure During a Trial of Spinal Cord Stimulation: Theories as to a Possible Connection, Pain Physician, 11(5): 681-686 (2008).

* cited by examiner

METHOD FOR TREATING HYPERTENSION VIA ELECTRICAL STIMULATION OF NEURAL STRUCTURES

RELATED APPLICATION DATA

The present application claims the benefit under 35 U.S.C. §119 to U.S. provisional patent application Ser. No. 61/703,609, filed Sep. 20, 2012. The foregoing application is hereby incorporated by reference into the present application in its entirety.

FIELD OF THE INVENTION

The present invention relates to tissue stimulation systems, and more particularly, to electrical stimulation systems for treating hypertension in patients.

BACKGROUND OF THE INVENTION

Implantable neurostimulation systems have proven therapeutic in a wide variety of diseases and disorders. For example, Spinal Cord Stimulation (SCS) techniques, which directly stimulate the spinal cord tissue of the patient, have long been accepted as a therapeutic modality for the treatment of chronic neuropathic pain syndromes, and the application of spinal cord stimulation has expanded to include additional applications, such as angina pectoralis, peripheral vascular disease, and incontinence, among others. Spinal cord stimulation is also a promising option for patients suffering from motor disorders, such as Parkinson's Disease, Dystonia and essential tremor.

An implantable SCS system typically includes one or more electrode-carrying stimulation leads, which are implanted at a stimulation site in proximity to the spinal cord tissue of the patient, and a neurostimulator implanted remotely from the stimulation site, but coupled either directly to the stimulation lead(s) or indirectly to the stimulation lead(s) via a lead extension. The neurostimulation system may further include a handheld patient programmer to remotely instruct the neurostimulator to generate electrical stimulation pulses in accordance with selected stimulation parameters. The handheld programmer may, itself, be programmed by a technician attending the patient, for example, by using a Clinician's Programmer (CP), which typically includes a general purpose computer, such as a laptop, with a programming software package installed thereon.

Thus, programmed electrical pulses can be delivered from the neurostimulator to the stimulation lead(s) to stimulate or activate a volume of the spinal cord tissue. In particular, electrical stimulation energy conveyed to the electrodes creates an electrical field, which, when strong enough, depolarizes (or "stimulates") the neural fibers within the spinal cord beyond a threshold level, thereby inducing the firing of action potentials (APs) that propagate along the neural fibers to provide the desired efficacious therapy to the patient.

Hypertension is a health problem affecting millions of people, requiring considerable expenditure of medical resources as well as imposing significant burdens on those who suffer from this condition. Hypertension generally involves resistance to the free flow of blood within a patient's vasculature, often caused by reduced volume stemming from plaque, lesions, and the like. Because blood vessels do not permit easy flow, the patient's heart must pump at higher pressure. In addition, reduced cross-sectional area results in higher flow velocity. In consequence, a patient's blood pressure may enter into the range of hypertension i.e. greater than 140 mm Hg systolic/90 mm Hg diastolic.

It has been recognized that the kidneys play a key role in blood pressure regulation, and a number of hypertension treatment approaches have focused on the kidneys, providing a number of pharmaceutical compounds aimed at promoting blood to flow through these organs. One treatment option has been to destroy some or all of the nerves innervating the kidneys through ablation, a process in which an ablation electrode, carried in an instrument such as an endoscope, is introduced into a patient's vasculature and navigated to a position within the renal artery. Electrical energy, operating at radio frequencies, is applied to the electrode, resulting in destruction of the renal nerves. This process, of course, is irreversible and carries the possibility of undesirable side effects. The process is nonetheless effective in combating hypertension.

Thus, a need remains for a process that can ameliorate hypertension without permanently affecting the renal nervous system.

SUMMARY OF THE INVENTION

In accordance with another aspect of the present inventions, a neuromodulation system may include a sensor configured for sensing a parameter correlatable to blood pressure of a patient, modulation output circuitry configured for conveying electrical modulation energy to at least one electrode, and a controller/processor coupled to the sensor and the modulation output circuitry. The controller/processor is configured for comparing the sensed parameter to a first threshold and instructing the modulation output circuitry to convey the electrical modulation energy to the at least one electrode based on the comparison. If the sensed parameter comprises a sensed blood pressure, and the first threshold comprises a first threshold blood pressure (e.g., 140 mm Hg systolic/90 mm Hg diastolic), the controller/processor may be configured for instructing the modulation output circuitry to convey the electrical modulation energy to the electrode(s) if the sensed blood pressure is greater than the first threshold blood pressure. In one embodiment, the controller/processor may be configured for comparing the blood pressure sensed by the sensor to a second threshold blood pressure (e.g., a value less than the first threshold, e.g., in a range of 100-140 mm Hg systolic/60-90 mm Hg), and instructing the stimulation output circuitry to cease conveying the electrical modulation energy to the at least one electrode if the sensed blood pressure is less than the second threshold blood pressure. The neuromodulation system may include a biocompatible casing housing the modulation output circuitry and the controller/processor. Further, the neuromodulation system may include the electrode(s).

In accordance with another aspect of the present inventions, a method for treating a patient from chronic hypertension is provided. The method comprises applying electrical modulation energy to a neural target site, thereby modulating an afferent nerve fiber (e.g., evoking action potentials along the nerve fiber or blocking action potentials along the nerve fiber) innervating a kidney of the patient, thereby treating the chronic hypertension. The neural target site may, e.g., be located on the afferent nerve fiber, itself, or may be located on a nerve fiber (e.g., an efferent nerve fiber) that synapses to the afferent nerve fiber. The neural target site may be, e.g., located on a spinal cord of the patient (e.g., the dorsal column (DC) nerve fiber), a dorsal root (DR) nerve fiber, or a peripheral nerve fiber. The nerve fiber may be an automatic nerve fiber; e.g., a sympathetic nerve fiber, in which case, the neural target site may be located at an L1-L3 spinal level, or a parasympathetic nerve fiber, in which case, the neural target site may be located at an S2-S4 spinal level. The electrical modulation energy may be epidurally applied to the target site on the afferent nerve fiber. In some embodiments, however, the electrical modulation energy may be applied transcutaneously to the target site. The patient may have a blood pressure greater than 140 mm Hg systolic/90 mm Hg diastolic prior to the application of the modulation energy to the target site on the afferent nerve fiber. The patient may have a blood pressure in the range of 100-140 mm Hg systolic/60-90 mm Hg diastolic during the application of the modulation energy to the target site on the afferent nerve fiber.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
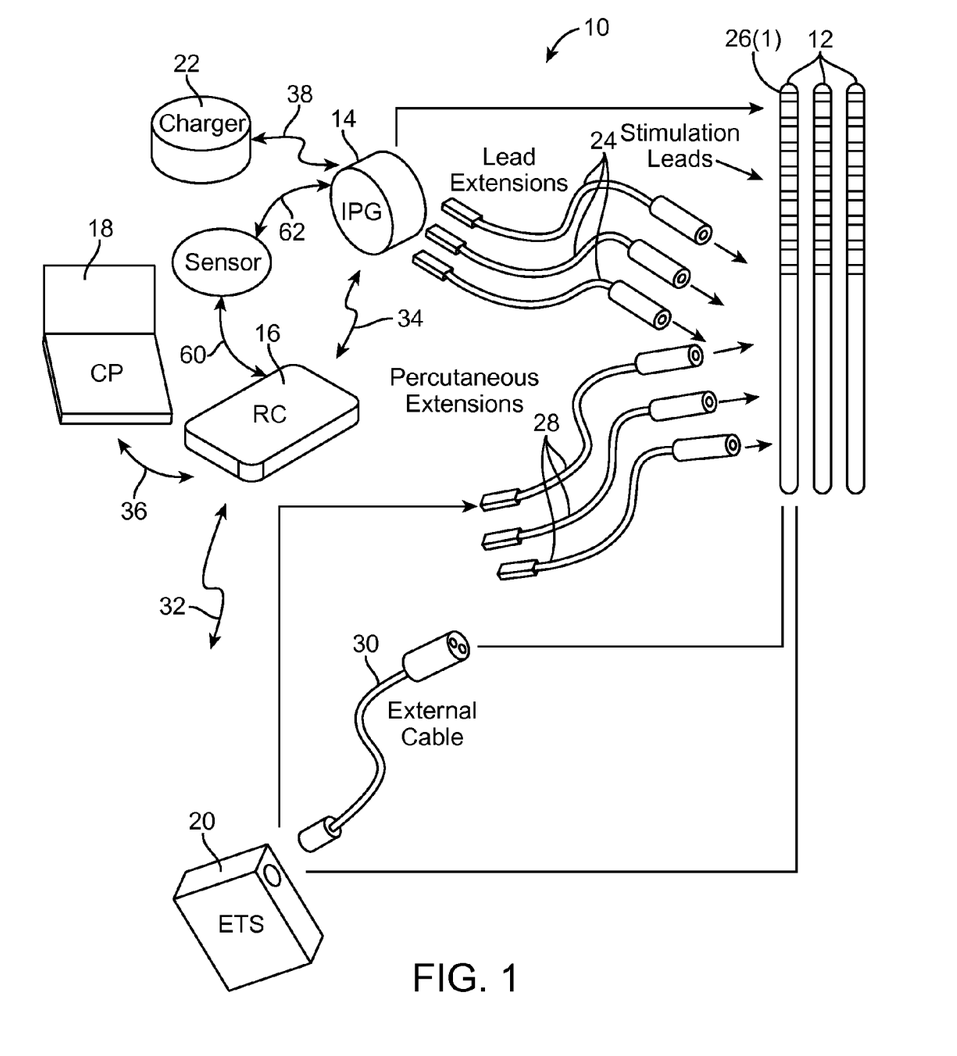
FIG. 1 is a plan view of a neuromodulation system constructed in accordance with one embodiment of the present inventions.

Turning first to FIG. 1, an exemplary neuromodulation system 10 generally comprises a plurality of modulation leads 12 (in this case, three), an implantable pulse generator (IPG) 14 (or alternatively RF receiver-stimulator), an external remote control (RC) 16, a Clinician's Programmer (CP) 18, an External Trial Stimulator (ETS) 20, and an external charger 22.

Figure 2:
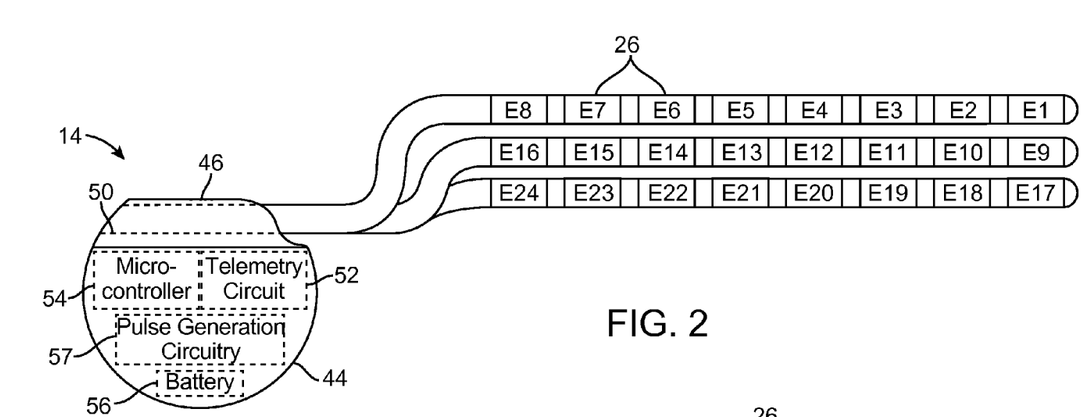
FIG. 2 is a plan view of an implantable pulse generator (IPG) and three percutaneous modulation leads used in the neuromodulation system of FIG. 1.

The IPG 14 is physically connected via one or more lead extensions 24 to the modulation leads 12, which carry a plurality of electrodes 26 arranged in an array. The modulation leads 12 are illustrated as percutaneous leads in FIG. 1, although as will be described in further detail below, a surgical paddle lead can be used in place of the percutaneous leads. As will also be described in further detail below, the IPG 14 includes pulse generation circuitry (FIG. 2) that delivers electrical modulation energy in the form of a pulsed electrical waveform (i.e., a temporal series of electrical pulses) to the array of electrodes 26 in accordance with a set of modulation parameters.

The ETS 20 may also be physically connected via the percutaneous lead extensions 28 and external cable 30 to the neuromodulation leads 12. The ETS 20, which has similar pulse generation circuitry as the IPG 14, also delivers electrical modulation energy in the form of a pulse electrical waveform to the array of electrodes 26 in accordance with a set of modulation parameters. The major difference between the ETS 20 and the IPG 14 is that the ETS 20 is a non-implantable device that is used on a trial basis after the neuromodulation leads 12 have been implanted and prior to implantation of the IPG 14, to test the responsiveness of the modulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neuromodulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. As will be described in further detail below, the CP 18 provides clinician detailed modulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18). The charger 22 may also communicate with the IPG 14 via a communications link 38.

The neuromodulation system 10 further includes a blood pressure sensor 58. A number of conventional pressure sensing devices and techniques are available to the art for sensing such factors. To sense blood pressure, for example, one could choose from among sensors bases on mechanical, piezoelectric, electromagnetic, or other technologies. The sensor 58 may be implanted within the patient's body, or one could employ a sensor 58 capable or remotely sensing the desired factor from a position outside the patient's body. In either instance, the sensor 58 communicates with the IPG 14 and the external RC 16 via bi-directional communication links 62 and 60, respectively, or via an electrical conductor (not shown).

These communication links may function via RF or other suitable technology. In alternative embodiments, other types of sensors that measure parameters correlatable to blood pressure (e.g., EKG using beat-to-beat (R-R) variability to globally assess autonomic tone) can be used.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 3:
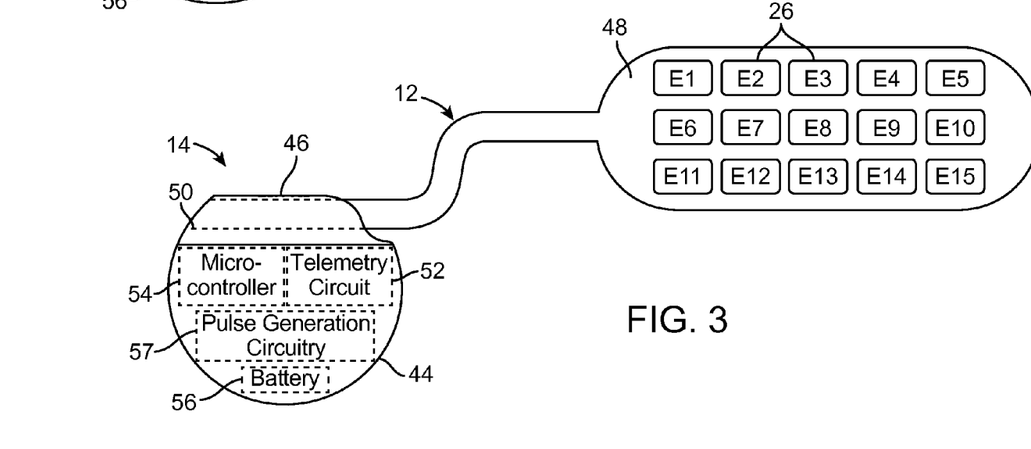
FIG. 3 is a plan view of an implantable pulse generator (IPG) and a surgical paddle lead used in the neuromodulation system of FIG. 1.

Referring now to FIG. 3, the external features of the modulation leads 12 and the IPG 14 will be briefly described. Each of the modulation leads 12 has eight electrodes 26 (respectively labeled E1-E8, E9-E16, and E17-E24). The actual number and shape of leads and electrodes will, of course, vary according to the intended application. Further details describing the construction and method of manufacturing percutaneous modulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Modulation and Method of Making Same," the disclosures of which are expressly incorporated herein by reference.

Figure 4:
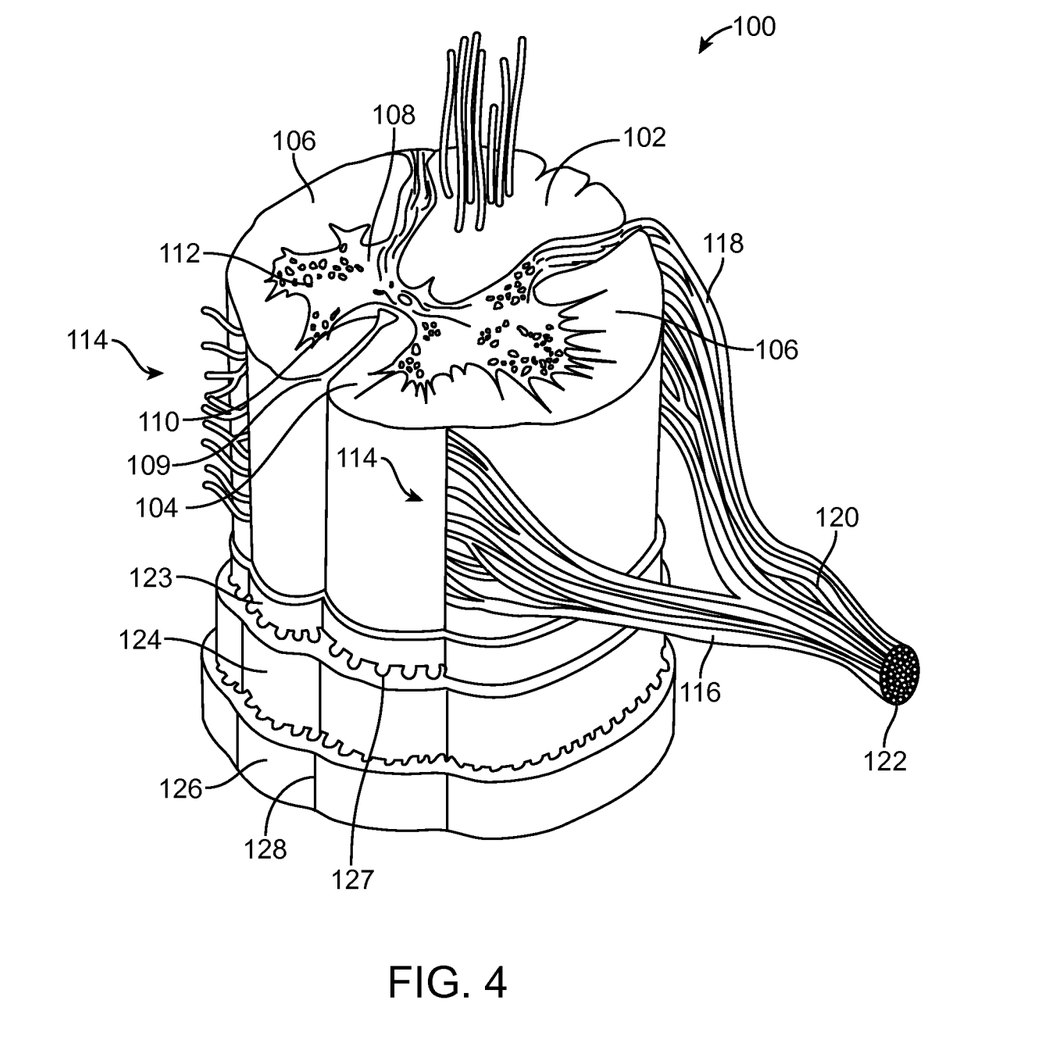
FIG. 4 is a pictorial/sectional view of the spinal cord and spinal nerves.

Alternatively, as illustrated in FIG. 4, the modulation lead 12 takes the form of a surgical paddle lead 48 on which electrodes 26 are arranged in a two-dimensional array in three columns (respectively labeled E1-E5, E6-E10, and E11-E15) along the axis of the modulation lead 12. In the illustrated embodiment, five rows of electrodes 26 are provided, although any number of rows of electrodes can be used. Each row of the electrodes 26 is arranged in a line transversely to the axis of the lead 12. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," the disclosure of which is expressly incorporated herein by reference.

In each of the embodiments illustrated in FIGS. 3 and 4, the IPG 14 includes an outer case 44 for housing the electronic and other components (described in further detail below). The outer case 44 is composed of an electrically conductive, biocompatible material, such as titanium, and forms a hermetically sealed compartment, wherein the internal electronics are protected from the body tissue and fluids. In some cases, the outer case 44 may serve as an electrode. The IPG 14 further comprises a connector 46 to which the proximal ends of the modulation leads 12 mate in a manner that electrically couples the electrodes 26 to the internal electronics (described in further detail below) within the outer case 44. To this end, the connector 46 includes one or more ports (three ports 50 or three percutaneous leads or one port for the surgical paddle lead) for receiving the proximal end(s) of the modulation lead(s) 12. In the case, where the lead extensions 24 (shown in FIG. 1) are used, the port(s) 50 may instead receive the proximal ends of such lead extensions 24.

Further, IPG 14 may include electronic components such as a telemetry circuit 52, a microcontroller 54, a battery 56, and other suitable components known to those skilled in the art. The microcontroller 54 executes a suitable program stored in memory (not shown), for directing and controlling the neuromodulation performed by IPG 14. Telemetry circuitry 52 (including antenna is configured for receiving programming data (e.g., the operating program and/or neuromodulation parameters) from the RC 16 in an appropriate modulated carrier signal, and demodulating the carrier signal to recover the programming data, which programming data is then stored in memory. The battery 56, which may be a rechargeable lithium-ion or lithium-ion polymer battery, provides operating power to IPG 14.

In addition, the IPG 14 includes pulse generation circuitry 57 that provides electrical conditioning and modulation energy in the form of a pulsed electrical waveform to the electrode array 26 in accordance with a set of modulation parameters programmed into the IPG 14. Such modulation parameters may comprise electrode combinations, which define the electrodes that are activated as anodes (positive), cathodes (negative), and turned off (zero), percentage of modulation energy assigned to each electrode of the array of electrodes 26 (fractionalized electrode configurations), and electrical pulse parameters, which define the pulse amplitude (measured in milliamps or volts depending on whether the IPG 14 supplies constant current or constant voltage to the array of electrodes 26), pulse width (measured in microseconds), pulse rate (measured in pulses per second), and burst rate (measured as the modulation on duration X and modulation off duration Y).

Electrical modulation will occur between two (or more) activated electrodes, one of which may be the IPG case 44. Simulation energy may be transmitted to the tissue in a monopolar or multipolar (e.g., bipolar, tripolar, etc.) fashion. Monopolar modulation occurs when a selected one of the lead electrodes 26 is activated along with the case 44 of the IPG 14, so that modulation energy is transmitted between the selected electrode 26 and the case 44. Bipolar modulation occurs when two of the lead electrodes 26 are activated as anode and cathode, so that modulation energy is transmitted between the selected electrodes 26. For example, an electrode on one lead 12 may be activated as an anode at the same time that an electrode on the same lead or another lead 12 is activated as a cathode. Tripolar modulation occurs when three of the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The modulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) modulation pulse and an anodic (positive) recharge pulse that is generated after the modulation pulse to prevent direct current charge transfer through the tissue, thereby avoiding electrode degradation and cell trauma. That is, charge is conveyed through the electrode-tissue interface via current at an electrode during a modulation period (the length of the modulation pulse), and then pulled back off the electrode-tissue interface via an oppositely polarized current at the same electrode during a recharge period (the length of the recharge pulse).

Referring now to FIG. 4, the portions of the spinal cord 100 that are relevant to the present inventions will be described. The spinal cord 100 is divided into three columns: the dorsal column 102, the ventral column 104, and the lateral columns 106. One lateral column lies on either side of the spinal cord 100. Similarly, the butterfly-shaped gray matter of the spinal cord 100 is divided into the dorsal horn 108, the ventral horn 110, and the lateral horn 112. A ventral median fissure 109 divides the spinal cord 100 into two lateral halves.

A group of motor nerve rootlets (ventral root nerve fibers) 114 branch off of the ventral horn 110 and combine to form the ventral root (VR) 116. Similarly, a group of sensory nerve rootlets (dorsal root (DR) nerve fibers) 118 branch off of the dorsal horn 108 and combine to form the dorsal root 120. The dorsal root 120 and the ventral root 116 combine to form the spinal nerve 122, which innervates peripheral regions (e.g., arms, legs, etc.) of the patient's body. It will be noted that symmetrical motor nerve rootlets, ventral root, sensory nerve rootlets, dorsal root, and spinal nerve are located on the opposite side of spinal cord 100, but these elements are omitted for simplicity. A number of spinal nerves branch off the spinal cord. In each patient, there are eight cervical spinal nerves designated C1-C8, twelve thoracic spinal nerves designated T1-T12, five lumbar spinal nerves designated L1-L5, and five sacral spinal nerves designated S1-S5.

Figure 6A:
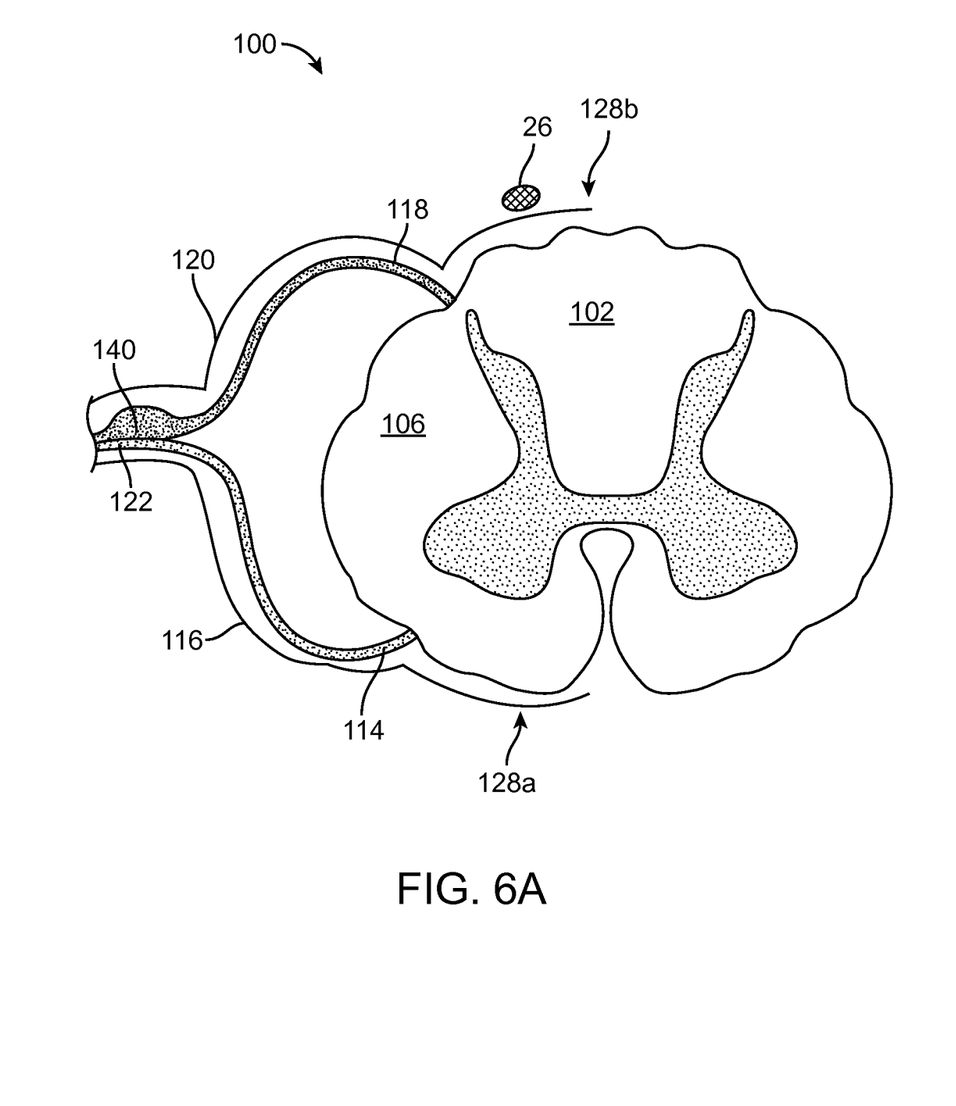
FIG. 6A is a schematic view showing a single-electrode arrangement relative to the spinal cord and spinal nerves in accordance with the present invention.

The spinal cord 100 is protected by three layers of connective tissue, the dura mater 126, the arachnoid 124, and the pia mater 123, collectively referred to as meninges. Epidural space 128 surrounds the dura mater 126, and subarachnoid space 127 lies under the arachnoid 124. The epidural space 128 may be topologically divided into two halves: a ventral epidural space 128a and a dorsal epidural space 128b (as shown in FIG. 6A).

The neuromodulation system 10 (shown in FIG. 1) may be employed to modulate various neural regions to treat hypertension. Specifically, the neuromodulation system 10 may be configured to modulate afferent nerve fibers innervating a patient's kidney, resulting in a reduction in the patient's blood pressure.

In particular, modulation of the afferent nerve fibers that innervate the kidney, modulation reduces sympathetic tone, which in turn has an electrical sympatholytic effect, producing a reduction in the patient's blood pressure. That is, modulation of the sympathetic nervous system may block action potentials that down-regulate the sympathetic nervous system, resulting in vasodilation, thus decreasing the patient's blood pressure. Alternatively, modulation of the parasympathetic nervous system may evoke action potentials that up-regulate the parasympathetic nervous system, resulting in vasodilation, thus decreasing the patient's blood pressure. Thus, it can appreciated that modulation of the autonomic nervous system (which includes both sympathetic and parasympathetic nerves) may decrease the patient's blood pressure.

Three variables affecting that method are the modulation location on the nerve fiber, the particular nerve fiber being chosen for modulation, and the particular modulation parameters used to either evoke action potentials or block action potentials along the nerve fiber. Notably, modulation of a nerve fiber at a pulse rate less 500 Hz may evoke action potentials in that nerve fiber, whereas modulation of a nerve fiber at a pulse rate greater than 1 KHz may block action potentials in that nerve fiber.

The neuromodulation system 10 may operate in a closed-loop manner to modulate the afferent nerve fibers that innervate the kidney based on sensed blood pressure. For example, the IPG 14 may obtain the detected blood pressure from the sensor 58 via the link 62 and compare it to both a first threshold (e.g., 140 mm Hg systolic/90 mm Hg diastolic) and a second threshold (e.g., somewhere in a range of 100-140 mm Hg systolic/60-90 mm Hg). If the comparison reveals that the detected blood pressure is above the first threshold, and the IPG 14 is currently not stimulating the afferent nerve fibers, the IPG 14 may automatically initiate modulation of the afferent nerve fibers. If the comparison shows that the detected blood pressure is below the second threshold (which may be equal to the first threshold), and the IPG 14 is current stimulating the afferent nerve fibers, the IPG 14 may automatically cease further modulation. Preferably, hysteresis may be built into the closed feedback loop, so that the IPG 14 does not rapidly initiate and cease modulation as the detected blood pressure varies around the first threshold. For example, the second threshold may be substantially less than the first threshold (e.g., by 5 or 10 mmHg).

Although control of the modulation based on the detected blood pressure has been described with respect to the IPG 14, it should be appreciated that an external control device may control the modulation based on the detected blood pressure. For example, the RC 16 may obtain the detected blood pressure from the sensor 58 via the link 60 and compare it to both the first and second threshold, and instruct the IPG 14 via the link 34 to either initiate modulation or cease modulation based on this comparison.

Figure 5:
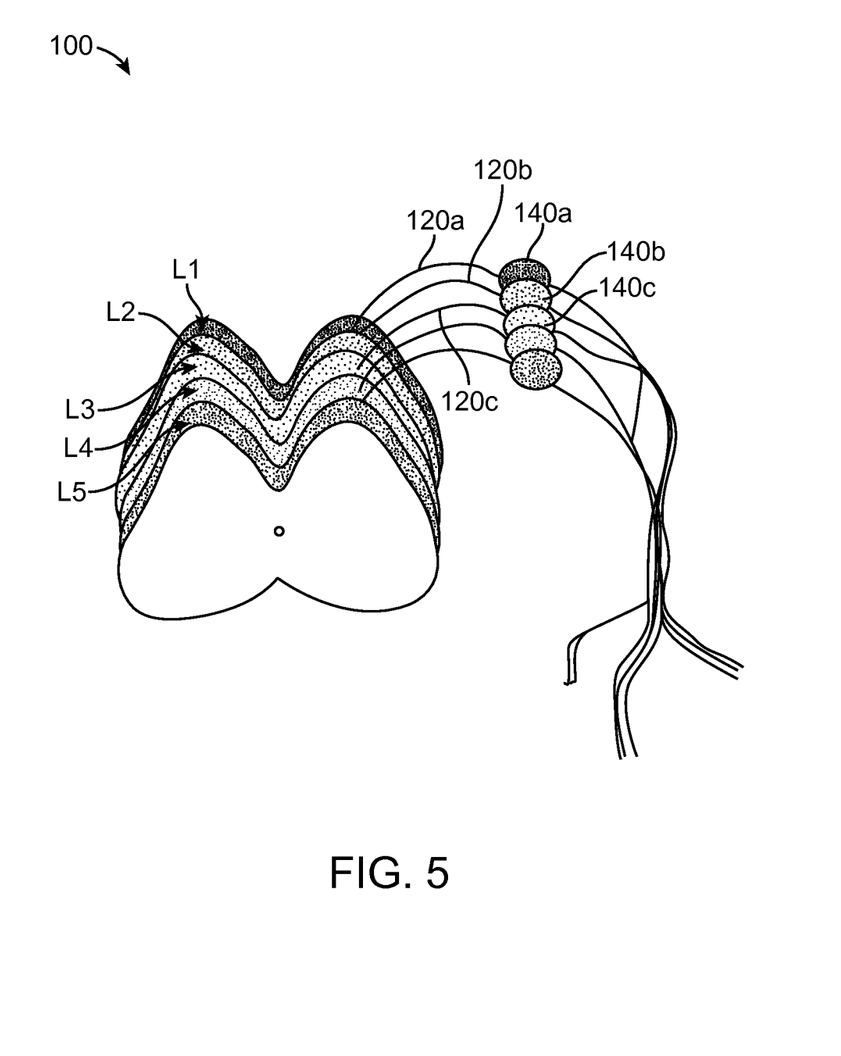
FIG. 5 is a schematic view showing various modulation regions relative to the spinal cord and spinal nerves in accordance with the present invention.

Referring to FIG. 5, it is known that sympathetic afferents from the kidneys converge at the inferior mesenteric ganglion (not shown) and then enter the spinal cord via the L1-L3 dorsal roots. As shown, dorsal roots 120a-120c emerge from lumbar vertebrae L1-L3 and pass through dorsal root ganglia 140a-140c. Among these peripheral nerve fibers are afferent fibers that go on to innervate the kidneys Thus, preferred methods of the present invention employ one or more of the electrodes 26 positioned to block action potentials in afferent nerve fibers in the dorsal column, the dorsal roots, and/or peripheral nerves associated with the L1-L3 vertebra. The modulation regime associated with electrodes 26 are designed to sufficiently modulate the dorsal column, dorsal roots, and/or peripheral nerves, as will be understood by those of skill in the art.

Figure 6B:
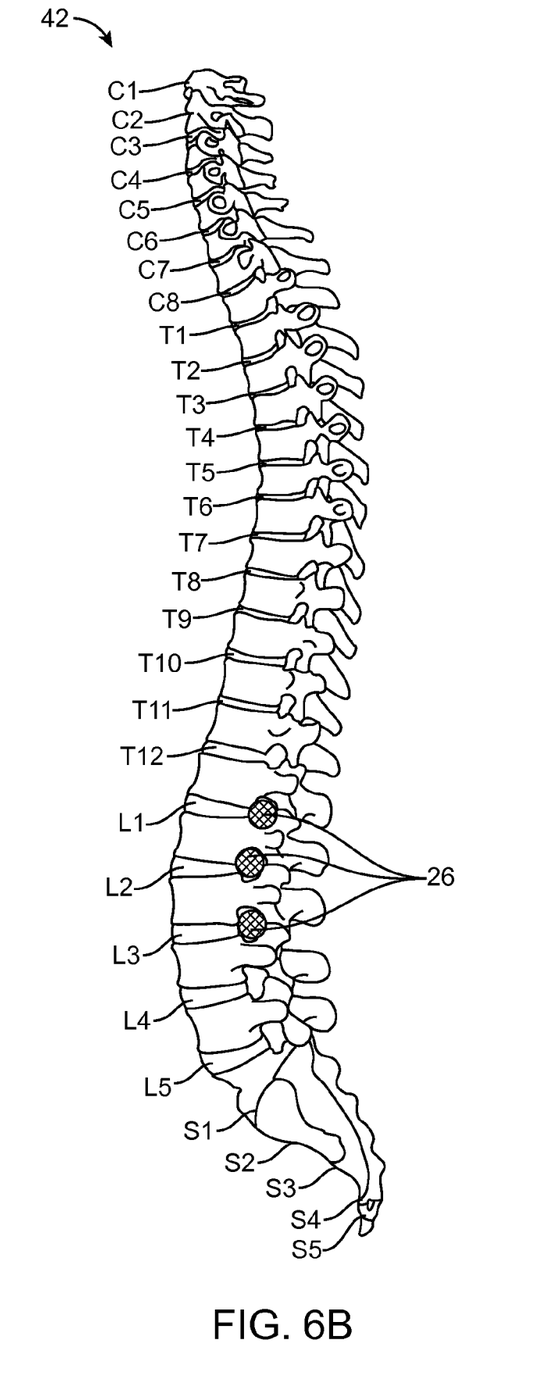
FIG. 6B is a schematic view showing the spinal column, showing the positioning of electrodes in accordance with the present invention.

For example, as shown in FIGS. 6A and 6B, one or more modulation electrodes 26 may be located within the dorsal epidural space 128b adjacent to the respective L1-L3 vertebra of the dorsal column 102. As another example, a modulation electrode 26 may be located near the dorsal root nerve fiber 118, positioned toward the dorsal root ganglia 140, as shown in FIG. 7.

Figure 7:
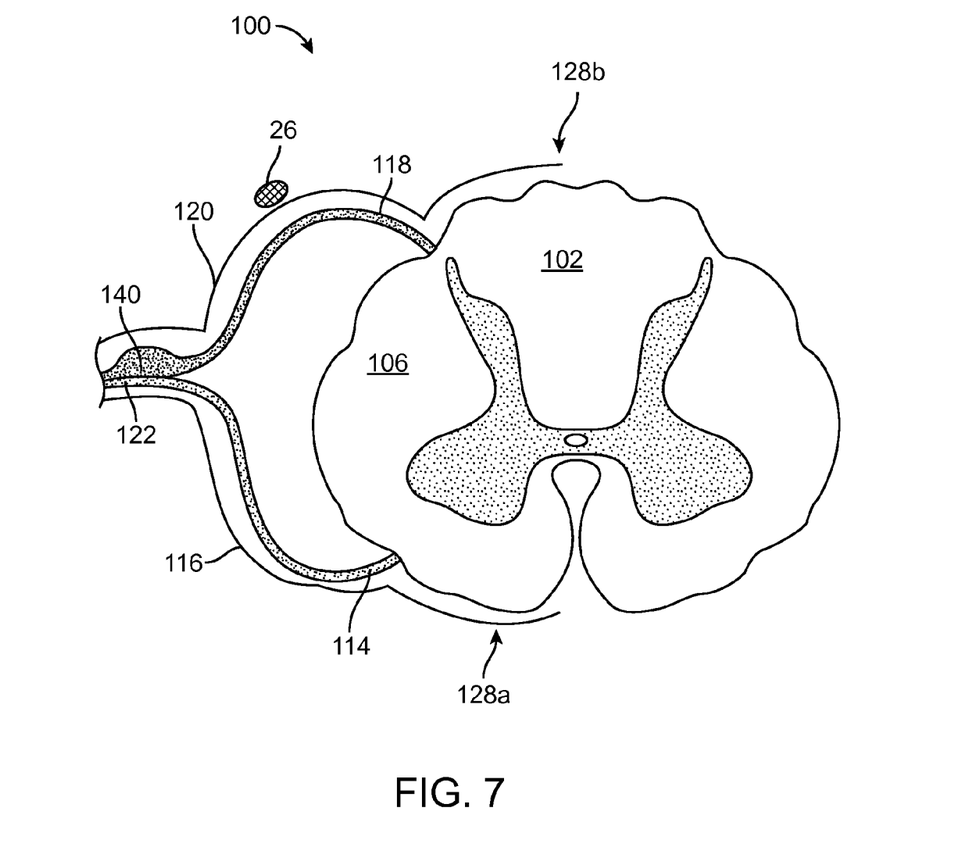
FIG. 7 is a schematic view showing another single-electrode arrangement relative to the spinal cord and spinal nerves in accordance with the present invention.
Figure 8:
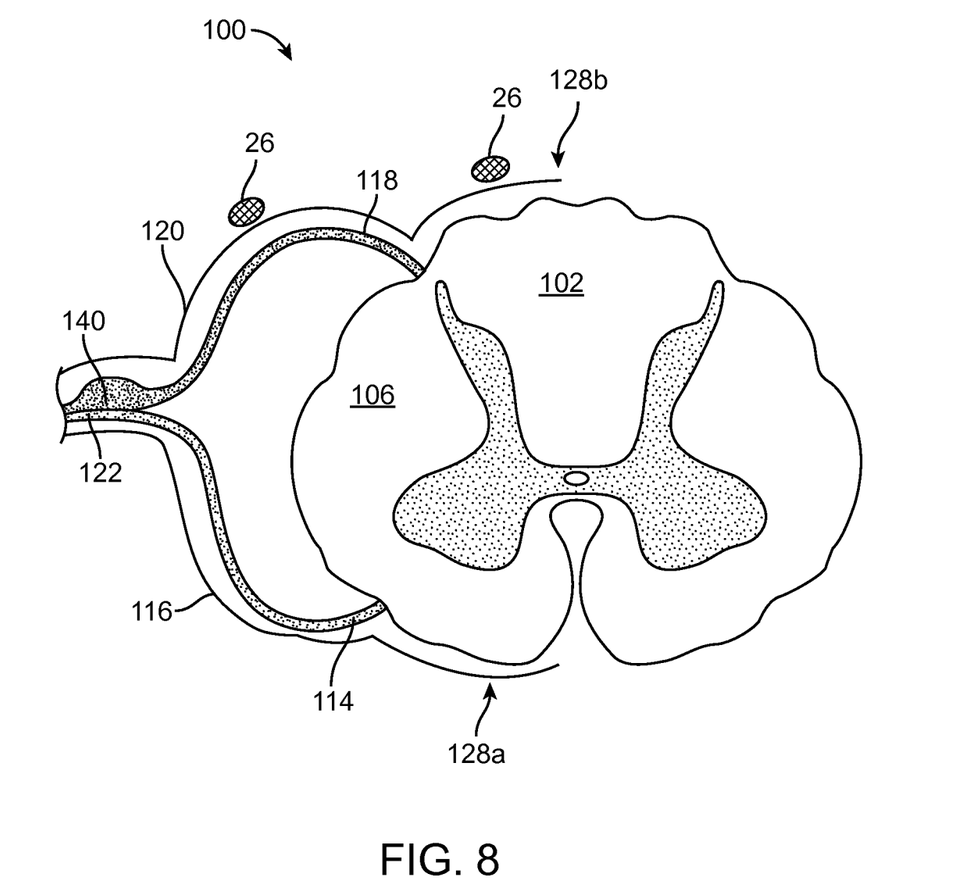
FIG. 8 is a schematic view showing a double-electrode arrangement relative to the spinal cord and spinal nerves in accordance with the present invention.

In contrast to FIGS. 6 and 7, which either locates the electrode or electrodes 26 adjacent the dorsal column 102 (FIG. 6) or adjacent the dorsal root nerve fiber 118 (FIG. 7), two modulation electrodes 26 are respectively located near the dorsal column 102 and the dorsal root nerve fiber 118 as shown in FIG. 8. This arrangement of electrodes may be configured to modulate the two regions simultaneously or in alternating fashion. Here, dorsal column electrode 306 is positioned in relatively close proximity to the DR 120, and the dorsal root nerve fiber electrode 308 is positioned close to the dorsal root ganglion 140 in the epidural space 128b.

Figure 9:
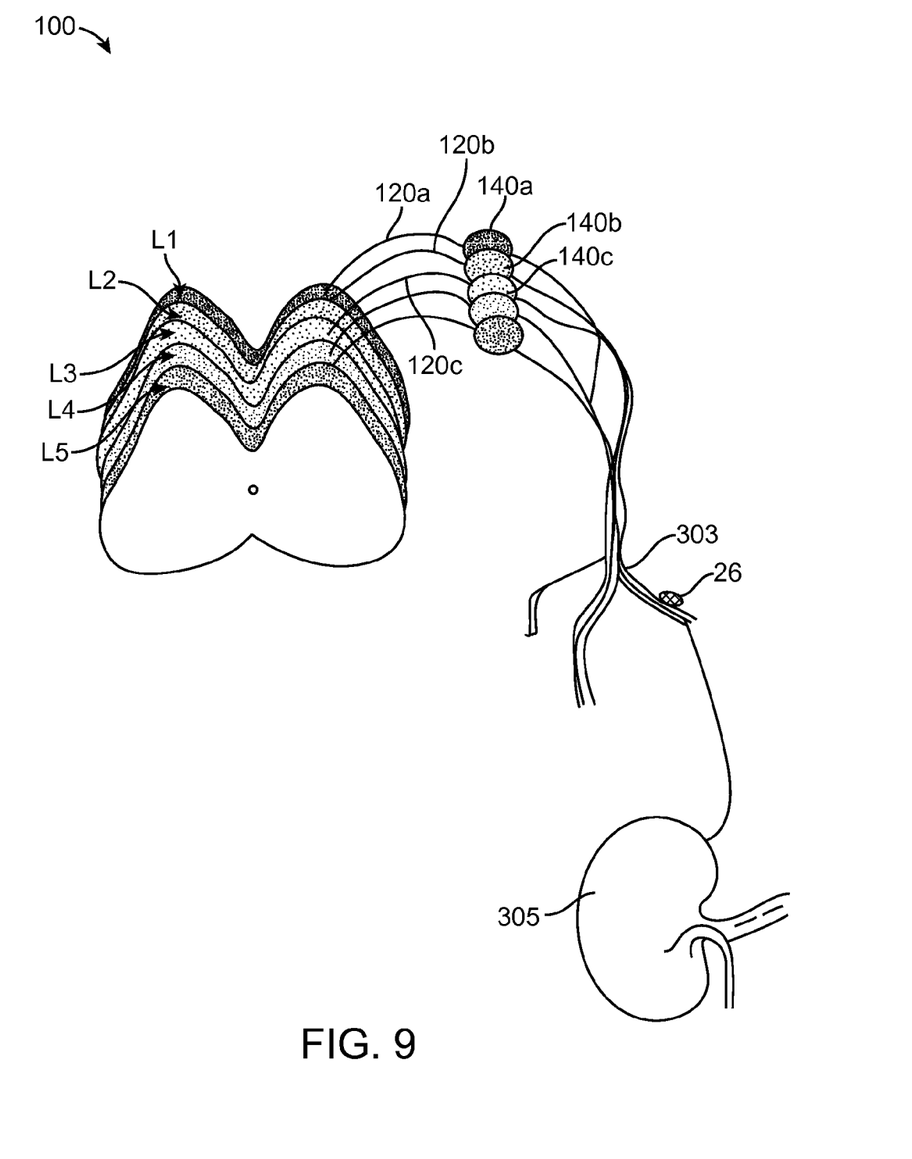
FIG. 9 is a schematic view showing a single-electrode arrangement near peripheral nerves in accordance with the present invention.

As another example shown in FIG. 9, an electrode 26 may be located near the peripheral nerve fiber 303. The peripheral nerve 303 innervates kidney 305, and the electrode 26 is positioned in a suitable location beyond dorsal root ganglion 140.

Alternatively, it is known that parasympathetic afferents from the kidneys converge at the pelvic nerve and then enter the spinal cord via the S2-S4 dorsal roots. Thus, preferred methods of the present invention employ one or more of the electrodes 26 positioned to evoke action potentials in afferent nerve fibers in the dorsal column, the dorsal roots, and/or peripheral nerves associated with the S2-S4 vertebra. The modulation regime associated with electrodes 26 are designed to sufficiently modulate the dorsal column, dorsal roots, and/or peripheral nerves, as will be understood by those of skill in the art.

Although the particular neural target site has been described as being located on the afferent nerve fiber innervating the kidney, it should be appreciated that the neural target site can be located on any nerve fiber (whether afferent or efferent) that synapses to the afferent nerve fiber that innervating the kidney. If the neural target site is located on an efferent nerve fiber, post-synaptic influence, as well as, perhaps, retrograde conduction of action potentials via efferent nerves, may result in the afferent nerve fibers innervating the kidneys; e.g., via reflex action through the spinal cord.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neuromodulation system, comprising:
   a sensor configured for sensing a blood pressure of a patient;
   modulation output circuitry configured for conveying electrical modulation energy to at least one electrode; and
   a controller/processor coupled to the sensor and the modulation output circuitry, the controller/processor configured for comparing the sensed blood pressure to a first threshold, instructing the modulation output circuitry to convey the electrical modulation energy to the at least one electrode if the sensed blood pressure is greater than the first threshold blood pressure, comparing the sensed blood pressure to a second threshold blood pressure, and instructing the modulation output circuitry to cease conveying the electrical modulation energy to the at least one electrode if the sensed blood pressure is less than the second threshold blood pressure.

2. The neuromodulation system of claim 1, wherein the first threshold blood pressure is 140 mm Hg systolic/90 mm Hg diastolic.

3. The neuromodulation system of claim 1, wherein the second threshold blood pressure is less than the first threshold blood pressure.

4. The neuromodulation system of claim 3, wherein the second threshold blood pressure is in the range of 100-140 mm Hg systolic/60-90 mm Hg.

5. The neuromodulation system of claim 1, further comprising a biocompatible casing housing the modulation output circuitry and the controller/processor.

6. The neuromodulation system of claim 1, further comprising the at least one electrode.

7. A method for treating a patient suffering from chronic hypertension using the neuromodulation system of claim 1, wherein the at least one electrode is adjacent a neural target site, the method comprising:
   sensing the blood pressure;
   comparing the sensed blood pressure to the first threshold;
   applying electrical modulation energy from the neuromodulation system to the neural target site if the sensed blood pressure is greater than the first threshold blood pressure, thereby modulating an afferent nerve fiber innervating a kidney of the patient, thereby treating the chronic hypertension;
   comparing the sensed blood pressure to a second threshold blood pressure; and
   ceasing applying electrical modulation energy from the neuromodulation system to the neural target site if the sensed blood pressure is less than the second threshold blood pressure.

8. The method of claim 7, wherein the neural target site is located on the afferent nerve fiber.

9. The method of claim 7, wherein the neural target site is located on an efferent nerve fiber that synapses to the afferent nerve fiber.

10. The method of claim 7, wherein the neural target site is on a spinal cord of the patient.

11. The method of claim 10, wherein the neural target site is on a dorsal column (DC) nerve fiber.

12. The method of claim 7, wherein the neural target site is on a dorsal root (DR) nerve fiber.

13. The method of claim 7, wherein the neural target site is on a peripheral nerve fiber.

14. The method of claim 7, wherein the modulating the afferent nerve fiber comprises evoking action potentials along the afferent nerve fiber.

15. The method of claim 7, wherein the modulating the afferent nerve fiber comprises blocking action potentials along the afferent nerve fiber.

16. The method of claim 7, wherein the afferent nerve fiber is an autonomic nerve fiber.

17. The method of claim 7, wherein the afferent nerve fiber is a sympathetic nerve fiber.

18. The method of claim 17, wherein the neural target site is located at an L1-L3 spinal level.

19. The method of claim 7, wherein the afferent nerve fiber is a parasympathetic nerve fiber.

20. The method of claim 19, wherein the neural target site is located at an S2-S4 spinal level.

21. The method of claim 7, wherein the electrical modulation energy is epidurally applied to the target site on the afferent nerve fiber.

22. The method of claim 7, wherein the electrical modulation energy is transcutaneously applied to the target site.

23. The method of claim 7, wherein the patient has a blood pressure greater than 140 mm Hg systolic/90 mm Hg diastolic prior to the application of the modulation energy to the target site on the afferent nerve fiber.

24. The method of claim 23, wherein the patient has a blood pressure in the range of 100-140 mm Hg systolic/60-90 mm Hg diastolic during the application of the modulation energy to the target site on the afferent nerve fiber.

25. The neuromodulation system of claim 1, wherein the controller/processor is configured for instructing the modulation output circuitry to convey the electrical modulation energy to the at least one electrode only if the electrical modulation energy is not being currently conveyed to the at least one electrode and if the sensed blood pressure is greater than the first threshold blood pressure, and instructing the modulation output circuitry to cease conveying the electrical modulation energy to the at least one electrode only if the electrical modulation energy is currently being conveyed to the at least one electrode and if the sensed blood pressure is less than the second threshold blood pressure.

* * * * *